United States Patent [19]
Sarkozi

[11] Patent Number: 5,211,623
[45] Date of Patent: May 18, 1993

[54] SELF ADJUSTING, SOFT NECK SUPPORT COLLAR

[76] Inventor: Jeff Sarkozi, 13722 Belle Rive, Santa Ana, Calif. 92705

[21] Appl. No.: 925,098

[22] Filed: Aug. 6, 1992

[51] Int. Cl.⁵ .............................................. A61F 5/02
[52] U.S. Cl. .............................. 602/18; 128/DIG. 23; 128/403
[58] Field of Search .................... 602/17, 18, 2, 14; 128/DIG. 23, 402, 403; 2/44, 45

[56] References Cited

U.S. PATENT DOCUMENTS

| | | | |
|---|---|---|---|
| 1,473,506 | 11/1923 | Nessler | 128/403 X |
| 1,610,712 | 12/1926 | Schweinert | 128/402 |
| 2,250,840 | 7/1941 | Pomeranz | 128/DIG. 23 X |
| 2,366,989 | 1/1945 | Robertson | 128/402 X |
| 2,562,121 | 7/1951 | Poux | 128/402 X |
| 3,810,466 | 5/1974 | Rogers | 602/18 |
| 4,805,619 | 2/1989 | Swearingen | 128/402 X |
| 4,865,012 | 9/1989 | Kelley | 128/403 X |
| 5,029,577 | 7/1991 | Sarkozi | 602/18 |

FOREIGN PATENT DOCUMENTS 1126120 6/1982 Canada ................................ 128/402

Primary Examiner—Richard J. Apley
Assistant Examiner—B. Meindl
Attorney, Agent, or Firm—Willie Krawitz

[57] ABSTRACT

A soft neck support collar is disclosed comprising two detached, superposed tubular ring elements which are connected at their respective ends, and are insertably and retractably secured within a flexible and removable outer sleeve. The tubular ring elements contain a soft fill material, and the combined effect of the fill material together with their tubular configuration, enables the collar to appropriately adjust for lateral, forward and backward neck movements. In addition to restricting neck mobility, the collar will self adjust for neutral positioning of the chin and neck.

Use of the sleeve enables the use of a greater range of tubular sizes, and provides for adjustable configurations. When necessary or desired, the addition of one or more smaller tubular elements on either side of the tubular ring elements can impart greater stiffness to the ring elements for a given neck position. If desired, a heating and/or cooling element may be insertably secured into the sleeve and between the tubular elements, without requiring additional attachment means, and the heating and/or cooling element will also impart additional reinforcement to the tubular ring elements.

13 Claims, 1 Drawing Sheet

U.S. Patent     May 18, 1993     5,211,623

SELF ADJUSTING, SOFT NECK SUPPORT COLLAR

BACKGROUND OF THE INVENTION

This invention relates to a new and improved self adjustable, soft neck support collar which can mount a heating and/or cooling element while restraining lateral, forward and backward movement of the neck.

A wide variety of neck support collars are in the market, and typical collars are disclosed in U.S. Pat. Nos. 1,964,962 2,389,690; 2,806,471; 3,964,474; 4,582,051; 4,700,697; 4,708,129; 4,958,631; and, 5,029,577. Some of these patents describe devices which are air inflatable, and while these devices provide support for a user's neck, the described air inflatable devices are not self adjustable, since air is the supporting medium. Other of these patented devices have fairly complicated collars which are expensive, and still other devices require adjustable straps. Additional types of these patented devices may be inexpensive to produce, but are not suitable for high volume, mass production.

Various other patents describe soft, unitary, solid foam neck support collars, but fail to provide sufficient resiliency when the neck is at rest, and do not provide enough resistance to lateral, forward or backward bending of the neck. Also, solid foam neck support collars fail to provide a means to vary the resiliency of the neck support for a given neck position. Moreover, solid foam block materials in general tend to buckle about midway along their length due to the pressure caused by neck motion. Finally, none of the patented devices provide a means to vary the temperature of the neck support for the purpose of providing sustained cooling or heating of a patient's neck, without disrupting the support function of the collar.

It would be desirable to provide a soft neck support device which has a simple construction and is inexpensive to manufacture, and can easily be mass produced to reduce costs. Also, the device should impart suitable neck restraint, and should be self adjusting in the sense that as the user's neck moves away from an erect position, the neck support provides increasing resistance in the direction of neck motion, rather than buckling. The device should also be adjustable to provide a variable resistance at the patient's discretion for a given fixed neck position.

Preferably, the device should enable use of a temperature control element to heat or cool the neck, which can be easily insertable and removable from the device while functioning as an additional reinforcement. This temperature control element should not add significantly to the bulk of the support collar, while still maintaining a smooth contact surface therewith. It would also be advantageous if the temperature control element did not require any securing or attachment means to maintain its position in the support collar.

In Applicant's U.S. Pat. Nos. 4,958,631 and 5,029,577 a soft, tubular neck support collar is disclosed in which the tubes are sewn together, and function to support a patient's neck. However, once the tubular elements are sewn together, the user cannot change the size or orientation of the tubes, and hence if different sized elements are preferred, a new set of tubular elements must be purchased. This is not only expensive from the patient's standpoint, but the manufacturer and retailer also must stock a wider size range of tubular elements.

Also, it would be desirable to provide a reinforcement for the tubular elements of the neck support which can more closely control the neck support, and which can be readily removed, e.g., during a resting period, if necessary. Also, it would be desirable to provide a soft tubular neck support which easily and variably aligns the tubular elements.

THE INVENTION

According to the invention, there is provided an adjustable neck support collar, comprising two detached, superposed tubular elements connected at their respective ends, the tubular elements being insertable or removable from a flexible and removable outer sleeve. The tubular elements are sized and shaped to fit around a user's neck and contain a soft fill support material.

The upper tubular element is tapered at each end, either by manufacture or by use, so that upon closure, it defines an open shape which fits under the user's chin. The lower tubular element is stacked coincidentally with the upper element, so that when the ends of the lower tubular element are connected, they will close at the front of the neck. If desired, the lower tubular element can also be rotated relative to the upper element if a change in position of the lower closure relative to the upper closure becomes necessary.

In addition, one or more smaller tubular elements may be used on either side and between the upper and lower elements to impart additional resiliency for a given neck position, prevent the heating and/or cooling element from moving away from the portion of the cloth sleeve closest to the neck, and reduce the possibility of vertical or lateral displacement of the tubular elements.

The outer sleeve is sized to house the tubular elements of the neck support which may have various sizes and shapes, and the sleeve materials readily permit transfer of heat or cooling from a heating and/or cooling element to the user's neck. Also, the resiliency of the cloth sleeve maintains adequate coincidental alignment of the tubular elements. At the same time, this will enable rotational adjustment of the lower tubular element with respect to the upper tubular element, thereby allowing a change in position of the lower closure with respect to the upper closure. The outer sleeve may be typically a cloth manufactured of cotton, polyester, nylon, acrylic polymers, etc.

Commercially available heating and/or cooling elements may be employed, and are shaped so that they can: 1. be easily inserted and removed from the neck support; 2. provide a smooth, continuous contact along the outer sleeve and the individual tubes; 3. accommodate an electrical power source or similar device if needed; and, 4. impart stability and reinforcement to the neck support while not altering the relative position of the tubular elements or add significantly to the volume of the neck support.

The soft fill interior of the tubular neck support elements may include air, water, $CO_2$, cotton, nylon, acrylic polymers, polyester, fiber fill, loose gauze, foam, beads, chip foam, down, etc., and mixtures thereof. The soft fill material of the neck support elements permits the user's neck to be comfortably supported, and enables the configuration and weight of the chin and neck to be supported when at rest. When the neck and chin deviate from an erect position, they will deform the neck support without causing buckling. Also, the neck support will provide progressively increasing resistive support as the neck and chin increasingly deviate from an erect position, until little or no further movement occurs.

The use of an outer sleeve in conjunction with detached tubular supports will facilitate the replacement of a single tubular element if a different size is needed, rather than having to purchase a completely new neck support. Moreover, if a heating/cooling element is used, it can be inserted readily or retracted from the tubular elements without needing a special securing means or mounting system, irrespective if detached or connected tubular supports are employed.

DESCRIPTION OF THE PREFERRED EMBODIMENTS

Figure 1:
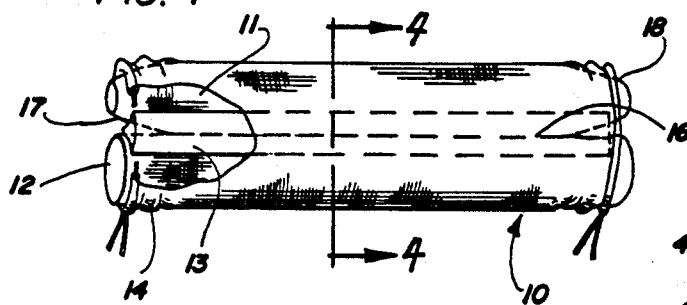
FIG. 1 is an external view in side elevation, partially broken away, to show the coincidentally aligned, detached tubular elements of the adjustable neck support of this invention together with an interfitted heating and/or cooling element.
Figure 2:
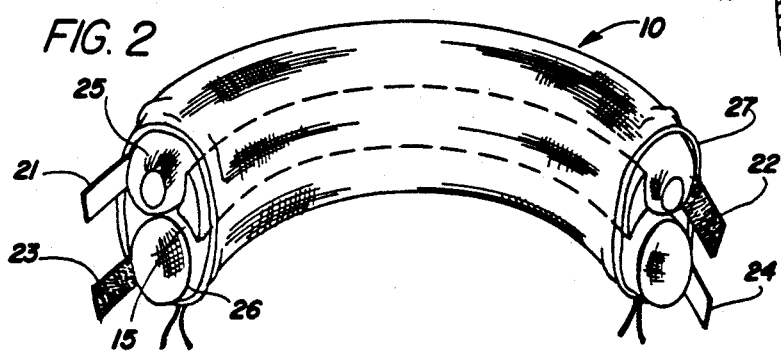
FIG. 2 is an external, perspective view of the neck support.

The adjustable neck support 10 of this invention is shown in FIGS. 1 and 2, and comprises upper and lower tubular elements 11 and 12, superposed and detached with respect to each other, and contained within a flexible and removable outer sleeve 14. A curved interface area 15 and a boundary line 16 is formed between the tubular elements, and a heating and/or cooling element 13 is interfitted along the interface area and boundary line.

Figure 6:
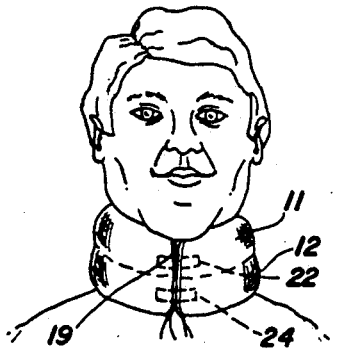
FIG. 6 is a front elevation view of the installed neck support.

As shown in FIGS. 1, 2 and 6, each end of the upper tubular element 11 is tapered 17 and 18 by manufacture or use, so that upon closure, a chin support 19 is formed where the ends meet. Thus, when the neck support 10 is installed, as shown in FIG. 6, the chin of the user fits into, and is supported in an appropriate position by the chin support. Moreover, when the lower tubular element 12 is closed at the front of the user's neck, it will then form a supporting ring. Hence, the user's chin is supported and fixed in position by the chin support, which in turn is supported by the lower tubular element. The soft fill of the interiors of the tubular elements is sufficiently flexible to self adjust for different shapes, sizes and weights of the user's neck and chin regions.

Figure 5:
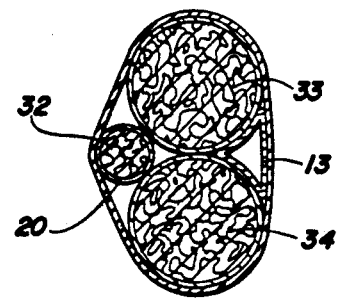
FIG. 5 is a cross sectional view of a modification of the neck support.

As shown in FIG. 5, if desired or necessary, one or two small size tubular elements 20, may be interfitted in the curved interface area 15 and along boundary line 16 between the tubular elements 11 and 12 to provide further support and to further secure them against vertical or lateral displacement. Also, if desired or necessary, a heating/cooling element 13 may be inserted in the curved interface area 15 and along boundary line 16 between the tubular elements 11 and 12.

In use, the respective ends of the tubular elements 11 and 12 are joined together by fasteners 21 and 22, 23 and 24, which may be constructed of VELCRO, hook elements, laces, etc. The fasteners 21-24 may also be placed on the outer sleeve 14 to achieve a similar closure effect.

The covering materials 25, 26, and 27 of the respective tubular elements 11 and 12 and outer sleeve 14 are preferably constructed of woven or knit cloth such as cotton, nylon, polyester, acrylic polymers, and blends of these, etc. Other materials may be used such as polyethylene, polypropylene, elastomers such as silicones, PVC, etc. The covering materials 27 of the outer sleeve 14 are selected to achieve a range of flexibility sufficient to house and accommodate different sizes and numbers of tubular elements and permit their rotational adjustment. At the same time, the covering materials 27 are manufactured with sufficient rigidity to prevent significant displacement of coincident alignment between the upper and lower tubular elements with respect to each other.

Figure 3:
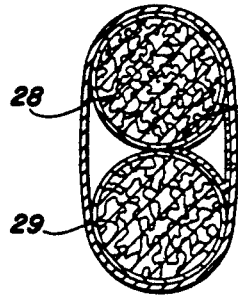
FIG. 3 is a cross sectional view, showing the tubular elements of the neck support joined by stitching.
Figure 4:
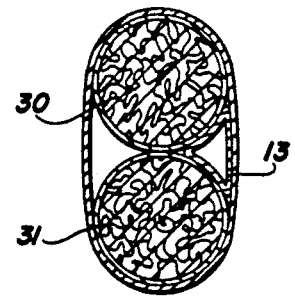
FIG. 4 is a cross sectional view of the neck support, taken along lines 4—4 of FIG. 1.

FIGS. 3, 4, and 5, show the tubular element interiors containing a soft fill 28-34, such as cotton, nylon, acrylic polymers, loose gauze, polyester, fiber fill, down, foam, chip foam, beads, and mixtures of these, and also $CO_2$, air, water, etc.

Coincidental displacement between the tubular elements may also be prevented by joining them with stitchings 35, and although this arrangement will impose certain restrictions on the position of the tubular elements, structural integrity is improved as compared with detached tubular elements. Moreover, it will still enable the insertion and retraction of a heating/cooling element, and smaller reinforcing tubular elements without requiring special securement means.

Figure 7:
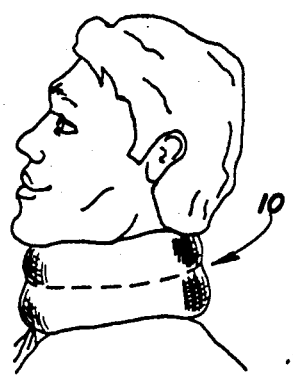
FIG. 7 is a side elevation view showing the neck support of FIG. 6.
Figure 8:
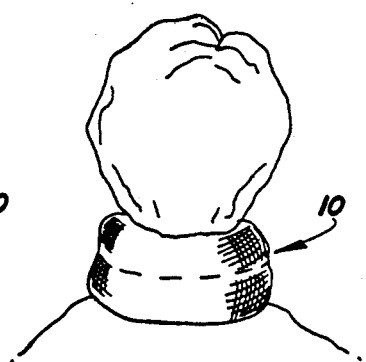
FIG. 8 is a rear elevation view of FIG. 6.

FIGS. 6, 7 and 8 illustrate the device when installed, and as shown in these three figures, the neck support 10 will maintain the neck aligned in an erect position.

Figure 9:
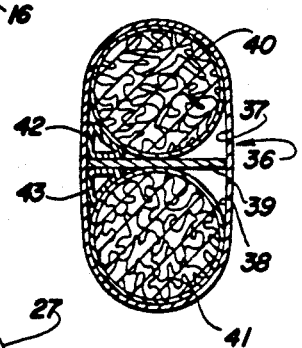
FIG. 9 is a cross sectional view of another embodiment of this invention.

The tubular sleeve may be compartmentalized to further reduce the horizontal and lateral displacement of the tubular elements, and FIG. 9 shows a tubular sleeve 36 defining compartments 37 and 38 which are separated by a boundary area 39 which may be a woven or knit cloth, plastic material, etc. Tubular elements 40 and 41 are separately partitioned within the respective compartments 37 and 38, and heating and/or cooling elements 42, 43 may be mounted along the interface of the tubular elements 40 and 41 and the boundary area 39, as required.

The tubular elements 11, 12 and 20 preferably vary in size from about ¼"-4" in diameter, and have differing lengths, depending on user neck sizes. Furthermore, their simple design makes them easy and inexpensive to manufacture, and suitable for high volume mass production. Also, the orientation of the tubular components with respect to each other permits them to self adjust to the user at rest, as well as during movement of the neck and chin without undue discomfort, considering the typical nature of the user's medical problem.

It will be appreciated that while the embodiments of this invention shown in FIGS. 1-4 and 6-8 are considered to represent the more usual mode of carrying out this invention, specific situations may arise where it would be preferred to enable the patient to have greater flexibility during treatment.

To achieve this purpose, additional tubular elements similar to the tubular element 20 can be added to the neck support, and the lower tubular-shaped element 12 can be rotated relative to the upper element 11 for user comfort and convenience in neck support.

As indicated, one of the unique features of this invention is the capability of maintaining a resilient support which increases as the user's neck and chin deviate from the erect position.

A second unique feature of this invention enables the extent of resilience to be varied by employing a particular fill material; by varying the size and packing density of the fill; by adjusting the diameter of the tubular elements; by varying the number of tubular elements employed; by varying the number of heating and/or cooling elements; and, by any combination thereof.

A third unique feature of this invention is that the addition of one or two tubular elements on either side of the tubular elements enable the user to more closely control the resiliency of the tubular elements.

Finally, a fourth unique feature of this invention is the capability of providing sustained homogeneous heating and cooling of the neck through the provision of easily insertable and removable heating/cooling elements. These elements are preferably designed and shaped to provide a relatively smooth, continuous contact between the entire length of the outer cloth sleeve and the tubular neck support, without significantly altering the volume of the neck support or relative position of the tubular elements.

I claim:

1. A self adjusting, soft, neck support collar, comprising:
   a.) an upper, tubular-shaped element providing an outer, covering material and an interior which contains a soft fill material, the tubular-shaped element defining ends which are adapted for closure under a user's chin by closure elements mounted at each end, to thereby form a ring which fits upwardly around the user's neck; and,
   b.) a lower, tubular-shaped element providing an outer covering material, and shaped to form an interior which contains a soft fill material, the lower, tubular-shaped element being adapted for closure at each end by closure elements to form a ring which fits around the lower portion of the user's neck, the upper and lower tubular elements being separate and distinct from each other so as to form a curved interface boundary line area therebetween and when the closure portions of each tubular element are connected, they will support the user's neck; whereby,
      i. the closure portion of the upper element and adjacent lower, tubular element define a chin support for the user; and,
      ii. the soft fill materials of the upper and lower tubular elements interiors function to: 1. impart a flexible support for the user's neck and chin which self adjusts for different shapes, sizes and weights of the user's neck and chin regions; 2. maintain a resilient support which increases as the user's neck and chin deviate from an erect position, during motion; and 3. self adjust to the user in a rest position; and,
   c.) a flexible and removable outer sleeve open on both ends and functioning to secure and stabilize the tubular elements and to enable the separate insertion and removal of upper or lower tubular elements of varying sizes while maintaining a resiliency sufficient to prevent vertical and lateral displacement of the tubular elements, and enabling horizontal rotation of the lower tubular element relative to the upper tubular element.

2. The neck support collar of claim 1, comprising a removable heating/cooling element shaped to interfit into the curved interface boundary area between the said upper and lower tubular elements, the heating/cooling element imparting additional stabilization to the tubular elements.

3. The neck support collar of claim 1, comprising at least one small sized tubular element interfitted into the curved interface boundary area between the tubular elements, thereby reducing vertical and lateral displacement of said tubular elements.

4. The neck support collar of claim 1, in which the outer covering of the tubular neck support elements is constructed of a woven or knit cloth selected from the class consisting of cotton, nylon, acrylic polymers, polyester, and blends thereof.

5. The neck support collar of claim 1, in which the outer covering of the tubular neck support elements is selected from the class consisting of cotton, nylon, acrylic polymers, polyesters, polyethylene, polypropylene, silicone elastomers, and PVC.

6. The neck support collar of claim 1, in which the soft fill interiors of the tubular neck support elements are selected from the class consisting of cotton, nylon, acrylic polymers, polyester, fiber fill, loose gauze, foam, beads, chip foam, down, air, water and $CO_2$, and mixtures thereof.

7. The neck support collar of claim 1, in which the outer sleeve is selected from the class consisting of cotton, nylon, acrylic polymers, polyesters, polyethylene, silicone elastomers, polypropylene, and PVC.

8. The neck support collar of claim 1, in which the tubular elements are separately partitioned in the said outer sleeve, and the tubular elements form an interface boundary with the partition.

9. The neck support of claim 1 in which the resilience of the tubular elements depends on the soft fill material being employed, by the size and packing density of the material, and by ring diameter.

10. The neck support of claim 1, in which the lower tubular element functions as a continuous, uniform, tubular-shaped ring upon closure.

11. The neck support of claim 1, in which the tubular elements are stacked in coincidence along their lengths, and both elements upon closure fit under the user's neck.

12. The neck support of claim 1, in which the tubular elements vary from about ½"–4" in diameter.

13. The neck support of claim 1, in which the upper tubular element defines tapered ends.

* * * * *